(12) United States Patent
Fu

(10) Patent No.: US 6,930,105 B2
(45) Date of Patent: Aug. 16, 2005

(54) TETRACYCLICAZAINDOLES AND INDOLINES HAVING 5-HT ACTIVITY

(75) Inventor: Jian-Min Fu, Kalamazoo, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 293 days.

(21) Appl. No.: 10/271,349

(22) Filed: Oct. 15, 2002

(65) Prior Publication Data

US 2003/0091505 A1 May 15, 2003

Related U.S. Application Data

(60) Provisional application No. 60/335,081, filed on Oct. 18, 2001.

(51) Int. Cl.[7] .................. A61K 31/5383; C07D 265/28

(52) U.S. Cl. ...................... 514/229.5; 544/99; 544/106

(58) Field of Search ................. 544/99, 106; 514/229.5

(56) References Cited

FOREIGN PATENT DOCUMENTS

| WO | WO 00/64899 | 11/2000 | | |
|----|-------------|---------|---|---|
| WO | WO 00/77002 | 12/2000 | | |
| WO | WO 00/77002 A1 | * 12/2000 | ......... | C07D/471/16 |

* cited by examiner

*Primary Examiner*—Joseph K. McKane
*Assistant Examiner*—Janet L Coppins
(74) *Attorney, Agent, or Firm*—Flynn, Thiel, Boutell & Tanis, P.C.

(57) ABSTRACT

The present invention provides compounds of Formula (I):

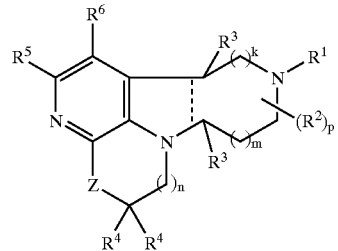

wherein $R^1$, $R^2$, $R^3$, $R^4$, $R^5$, and $R^6$, have any of the values defined in the specification, as well as pharmaceutical compositions comprising the compounds. The invention also provides therapeutic methods as well as processes and intermediates useful for preparing compounds of Formula (I). The compounds are 5-HT ligands and are useful for treating diseases wherein modulation of $5\text{-HT}_{2C}$ activity is desired.

54 Claims, No Drawings

TETRACYCLICAZAINDOLES AND INDOLINES HAVING 5-HT ACTIVITY

CROSS-REFERENCE TO RELATED APPLICATIONS

This application claims the benefit of U.S. provisional application Ser. No. 60/335,081 filed on Oct. 18, 2001, under 35 USC 119(e)(i), which is incorporated herein by reference in its entirety.

FIELD OF THE INVENTION

The present invention provides tetracyclicazaindoles and indolines, and more specifically, provides compounds of Formula (I) described herein below. These compounds are 5-HT$_{2C}$ ligands and are useful for treating diseases wherein modulation of 5-HT$_{2C}$ activity is desired.

BACKGROUND OF THE INVENTION

Serotonin (5-HT), a neurotransmitter, has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. R. W. Fuller, *Biology of Serotonergic Transmission*, ed. Neville V. Osborne, John Wiley and Sons (1982), p 221; D. J. Boullin, *Serotonin in Mental Abnormalities* 1, John Wiley and Sons (1978), p. 316; J. Barchas, et al., *Serotonin and Behavior*, Academic Press, New York, N.Y. (1973). Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, 5-HT receptor-specific agonists and antagonists are of interest for the treatment of a wide range of disorders, including anxiety, depression, hypertension, migraine, obesity, compulsive disorders, schizophrenia, autism, neurodegenerative disorders (e.g., Alzheimer's disease, Parkinson's Disease, and Huntington's chorea), and chemotherapy-induced vomiting. M. D. Gershon, et al., "5-Hydroxytryptamine and enteric neurones", in Chapter 11 of *The Peripheral Actions of 5-Hydroxytryptamine*, pages 247–273, Oxford University Press, (1989); P. R. Saxena, et al., *Journal of Cardiovascular Pharmacology*, 15: Supp. 7 (1990).

The major classes of serotonin receptors (5-HT$_{1-7}$) contain fourteen to eighteen separate receptors that have been formally classified. See Glennon, et al., *Neuroscience and Behavioral Reviews*, 14, 35 (1990); and D. Hoyer, et al., *Pharmacol. Rev.*, 46, 157–203 (1994). Recently discovered information regarding subtype identity, distribution, structure, and function suggests that it is possible to identify novel, subtype specific agents, having improved therapeutic profiles (e.g. fewer side effects).

For example, the 5-HT$_2$ family of receptors is made up of 5-HT$_{2A}$, 5-HT$_{2B}$, and 5-HT$_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three 5-HT$_2$ subtypes. The 5-HT$_{2B}$ and 5-HT$_{2A}$ receptors are widely distributed in the periphery, while the 5-HT$_{2C}$ receptor has been found only in the central nervous system, being highly expressed in many regions of the human brain. See G. Baxter, et al., *Trends in Pharmacol. Sci.*, 16, 105–110 (1995).

Subtype 5-HT$_2$A is associated with vasoconstriction, platelet aggregation, and bronchoconstriction. Subtype 5-HT$_{2C}$ is associated with diseases including depression, anxiety, obsessive compulsive disorder, panic disorders, phobias, psychiatric syndromes, and obesity. Very little is known about the pharmacological role of the 5-HT$_{2B}$ receptor. See Jenck et al., *Exp. Opin. Invest. Drugs*, 7, 1587–1599 (1998); Bos et al., *J. Med. Chem.*, 40, 2762–2769 (1997); Martin et al., *The Journal of Pharmacology and Experimental Therapeutics*, 286, 913–924 (1998); Bromidge et al., *J. Med. Chem.*, 41, 1598–1612 (1998); Kennett, *IDrugs*, 1, 456–470 (1998); and Dekeyne, et al., *Neuropharmacology*, 38, 415–423 (1999). ISAAC, *Drugs of the Future*, 26, 383–393 (2001).

International Patent Applications WO 00/77001, WO 00/77002, and WO 00/77010 disclose tetracyclic compounds that are reported to possess activity as serotonin agonists and antagonists.

There is currently a need for pharmaceutical agents that are useful to treat diseases and conditions that are associated with 5-HT receptors.

SUMMARY OF THE INVENTION

The invention provides novel compounds which demonstrate useful biological activity, and particularly activity as 5-HT$_{2C}$ ligands. Thus, the present invention provides a compound of Formula (I):

Formula I

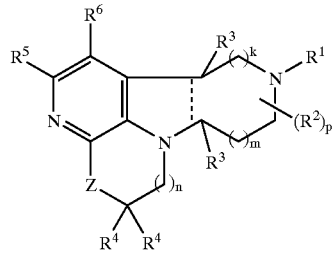

wherein Z is —CR$_a$R$_b$—, —C(=O)—, —O—, —S—, —SO—, —SO$_2$—, —N(R$_a$)—, —C(O)N(R$_a$)—, —N(R$_a$)C(O)—, —C(S)N(R$_a$)—, or —N(R$_a$)C(S)—;

the bond represented by - - - is a single or double bond;

R$^1$ is H, C$_{1-8}$alkyl, C$_{3-8}$cycloalkyl, or arylC$_{1-8}$alkylene-;

each R$^2$ is independently C$_{1-8}$ alkyl, aryl, arylC$_{1-8}$alkylene-, or OR$_a$;

each R$^3$ is absent or independently H, C$_{1-8}$ alkyl, arylC$_{1-8}$alkylene-, provided that each R$^3$ is absent when the bond represented by - - - is a double bond;

each R$^4$ is independently H, —F, C$_{1-8}$ alkyl, aryl, arylC$_{1-8}$alkylene-, heteroaryl, or heteroaryl(C$_{1-8}$)alkylene-;

R$^5$ and R$^6$ are each independently H, halo, —CN, —NO$_2$, —CF$_3$, —OCF$_3$, azido, —OR$_a$, —NR$_c$R$_d$, —C(=O)NR$_c$R$_d$, —C(=S)NR$_c$R$_d$, C$_{1-8}$ alkyl, C$_{3-8}$ cycloalkyl, aryl, arylC$_{1-8}$alkylene-, heteroaryl, heteroarylC$_{1-8}$alkylene-, amidinyl, guanidinyl, thioguanidinyl, or cyanoguanidinyl;

wherein any aryl or heteroaryl group of R$^1$, R$^2$, R$^3$, R$^4$, R$^5$, and R$^6$ is optionally substituted with one or more substituents, e.g., 1, 2, 3, or 4, independently selected from the following: halo, —OH, —CN, —NO$_2$, —CF$_3$, —OCF$_3$, $N_3$, $-S(O)_{0-2}C_{1-8}$alkyl, $-C_{1-8}$alkyl, $-C_{3-8}$cycloalkyl, $-OC_{1-8}$alkyl, phenyl, $-C_{1-8}$alkanoyl, $-C(=O)OR_a$, $-N(R_a)C(=O)NR_cR_d$, $-N(R_a)C(=O)OR_a$, $-C(=O)NR_cR_d$, $-C(=S)NR_cR_d$, $-SO_2NR_cR_d$, $-C_{1-8}$alkyl, $-NR_cR_d$, $-OPh$, tetrazolyl, triazolyl, amidinyl, guanidinyl, thioguanidinyl, and cyanoguanidinyl;

$R_a$ and $R_b$ are each independently H, $C_{1-8}$alkyl, $C_{3-8}$cycloalkyl, aryl, aryl($C_{1-8}$)alkylene-, heteroaryl, or heteroaryl($C_{1-8}$)alkylene-;

$R_c$ and $R_d$ are each independently H, $C_{1-8}$alkyl, $C_{3-8}$cycloalkyl, aryl, aryl($C_{1-8}$)alkylene-, heteroaryl, or heteroaryl($C_{1-8}$)alkylene-; or $R_c$ and $R_d$ together with the nitrogen to which they are attached form a pyrrolidine, piperidine, azepine, morpholine, thiomorpholine, thiomorpholine 1-oxide, or thiomorpholine 1,1-dioxide ring;

k is 1 or 2;
m is 0, 1, or 2;
n is 0, 1, 2, or 3;
p is 0, 1, 2, 3, 4, 5, 6, 7, 8, 9, or 10;
or a pharmaceutically acceptable salt thereof.

A specific compound of the invention is of Formula (II):

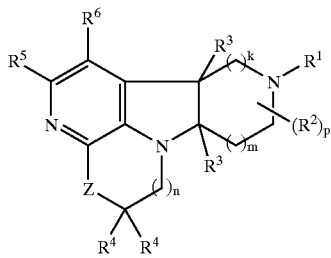

Formula II wherein Z is $-CR_aR_b-$, $-C(=O)-$, $-O-$, $-S-$, $-SO-$, $-SO_2-$, $-N(R_a)-$, $-C(O)N(R_a)-$, $-N(R_a)C(O)-$, $-C(S)N(R_a)-$, or $-N(R_a)C(S)-$;

$R^1$ is H, $C_{1-8}$alkyl, $C_{3-8}$cycloalkyl, or aryl$C_{1-8}$alkylene-;

each $R^2$ is independently $C_{1-8}$ alkyl, aryl, aryl$C_{1-8}$alkylene-, or $OR_a$;

each $R^3$ is independently H, $C_{1-8}$ alkyl or aryl$C_{1-8}$alkylene-;

each $R^4$ is independently H, $-F$, $C_{1-8}$ alkyl, aryl, aryl$C_{1-8}$alkylene-, heteroaryl, or heteroaryl($C_{1-8}$)alkylene-;

$R^5$ and $R^6$ are each independently H, halo, $-CN$, $-NO_2$, $-CF_3$, $-OCF_3$, azido, $-OR_a$, $-NR_cR_d$, $-C(=O)NR_cR_d$, $-C(=S)NR_cR_d$, $C_{1-8}$ alkyl, $C_{3-8}$ cycloalkyl, aryl, aryl$C_{1-8}$alkylene-, heteroaryl, heteroaryl$C_{1-8}$alkylene-, amidinyl, guanidinyl, thioguanidinyl, or cyanoguanidinyl;

wherein any aryl or heteroaryl group of $R^1, R^2, R^3, R^4, R^5$, and $R^6$ is optionally substituted with one or more substituents, e.g., 1, 2, 3, or 4, independently selected from the following: halo, $-OH$, $-CN$, $-NO_2$, $-CF_3$, $-OCF_3$, $N_3$, $-S(O)_{0-2}C_{1-8}$alkyl, $-C_{1-8}$alkyl, $-C_{3-8}$cycloalkyl, $-OC_{1-8}$alkyl, phenyl, $-C_{1-8}$alkanoyl, $-C(=O)OR_a$, $-N(R_a)C(=O)NR_cR_d$, $-N(R_a)C(=O)OR_a$, $-C(=O)NR_cR_d$, $-C(=S)NR_cR_d$, $-SO_2NR_cR_d$, $-C_{1-8}$alkyl, $-NR_cR_d$, $-OPh$, tetrazolyl, triazolyl, amidinyl, guanidinyl, thioguanidinyl, and cyanoguanidinyl;

$R_a$ and $R_b$ are each independently H, $C_{1-8}$alkyl, $C_{3-8}$cycloalkyl, aryl, aryl($C_{1-8}$)alkylene-, heteroaryl, or heteroaryl($C_{1-8}$)alkylene-;

$R_c$ and $R_d$ are each independently H, $C_{1-8}$alkyl, $C_{3-8}$cycloalkyl, aryl, aryl($C_{1-8}$)alkylene-, heteroaryl, or heteroaryl($C_{1-8}$)alkylene-; or $R_c$ and $R_d$ together with the nitrogen to which they are attached form a pyrrolidine, piperidine, azepine, morpholine, thiomorpholine, thiomorpholine 1-oxide, or thiomorpholine 1,1-dioxide ring;

k is 1 or 2;
m is 0, 1, or 2;
n is 0, 1, 2, or 3;
p is 0, 1, 2, 3, 4, 5, 6, 7, 8, 9, or 10;
or a pharmaceutically acceptable salt thereof.

A specific compound of the invention is of Formula (III):

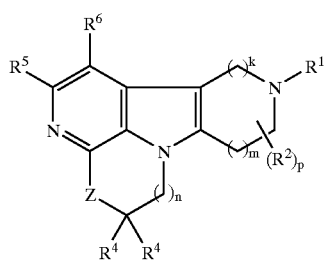

Formula III wherein Z is $-CR_aR_b-$, $-C(=O)-$, $-O-$, $-S-$, $-SO-$, $-SO_2-$, $-N(R_a)-$, $-C(O)N(R_a)-$, $-N(R_a)C(O)-$, $-C(S)N(R_a)-$, or $-N(R_a)C(S)-$;

$R^1$ is H, $C_{1-8}$alkyl, $C_{3-8}$cycloalkyl, or aryl$C_{1-8}$alkylene-;

each $R^2$ is independently $C_{1-8}$ alkyl, aryl, aryl$C_{1-8}$alkylene-, or $OR_a$;

each $R^4$ is independently H, $-F$, $C_{1-8}$ alkyl, aryl, aryl$C_{1-8}$alkylene-, heteroaryl, or heteroaryl($C_{1-8}$)alkylene-;

$R^5$ and $R^6$ are each independently H, halo, $-CN$, $-NO_2$, $-CF_3$, $-OCF_3$, azido, $-OR_a$, $-NR_cR_d$, $-C(=O)NR_cR_d$, $-C(=S)NR_cR_d$, $C_{1-8}$ alkyl, $C_{3-8}$ cycloalkyl, aryl, aryl$C_{1-8}$alkylene-, heteroaryl, heteroaryl$C_{1-8}$alkylene-, amidinyl, guanidinyl, thioguanidinyl, or cyanoguanidinyl;

wherein any aryl or heteroaryl group of $R^1, R^2, R^3, R^4, R^5$, and $R^6$ is optionally substituted with one or more substituents, e.g., 1, 2, 3, or 4, independently selected from the following: halo, $-OH$, $-CN$, $-NO_2$, $-CF_3$, $-OCF_3$, $N_3$, $-S(O)_{0-2}C_{1-8}$alkyl, $-C_{1-8}$alkyl, $-C_{3-8}$cycloalkyl, $-OC_{1-8}$alkyl, phenyl, $-C_{1-8}$alkanoyl, $-C(=O)OR_a$, $-N(R_a)C(=O)NR_cR_d$, $-N(R_a)C(=O)OR_a$, $-C(=O)NR_cR_d$, $-C(=S)NR_cR_d$, $-SO_2NR_cR_d$, $-C_{1-8}$alkyl, $-NR_cR_d$, $-OPh$, tetrazolyl, triazolyl, amidinyl, guanidinyl, thioguanidinyl, and cyanoguanidinyl;

$R_a$ and $R_b$ are each independently H, $C_{1-8}$alkyl, $C_{3-8}$cycloalkyl, aryl, aryl($C_{1-8}$)alkylene-, heteroaryl, or heteroaryl ($C_{1-8}$) alkylene-;

$R_c$ and $R_d$ are each independently H, $C_{1-8}$alkyl, $C_{3-8}$cycloalkyl, aryl, aryl($C_{1-8}$)alkylene-, heteroaryl, or heteroaryl($C_{1-8}$)alkylene-; or $R_c$ and $R_d$ together with the nitrogen to which they are attached form a pyrrolidine, piperidine, azepine, morpholine, thiomorpholine, thiomorpholine 1-oxide, or thiomorpholine 1,1-dioxide ring;

k is 1 or 2;
m is 0, 1, or 2;
n is 0, 1, 2, or 3;
p is 0, 1, 2, 3, 4, 5, 6, 7, 8, 9, or 10;
or a pharmaceutically acceptable salt thereof.

Preferred compounds of the invention are:
2-phenyl-5,6,6b,7,8,9,10,10a-octahydro-4-oxa-3,6a,9-triaza-fluoranthene;
2-(2,6-difluorophenyl)-5,6,6b,7,8,9,10,10a-octahydro-4-oxa-3,6a,9-triaza-fluoranthene;
2-(2,4-dichlorophenyl)-5,6,6b,7,8,9,10,10a-octahydro-4-oxa-3,6a,9-triaza-fluoranthene;
2-phenyl-6,7,7b,8,9,10,11,11a-octahydro-5H-4-thia-3,7a,10-triaza-cyclohepta[jk]fluorene;
2-(2,4-dichlorophenyl)-6,7,7b,8,9,10,11,11a-octahydro-5H-4-thia-3,7a,10-triaza-cyclohepta[jk]fluorene; and 2-(2,6-difluorophenyl)-6,7,7b,8,9,10,11,11a-octahydro-5H-4-thia-3,7a,10-triaza-cyclohepta[jk]fluorene; or a pharmaceutically acceptable salt thereof.

In another aspect, the present invention also provides:

a pharmaceutical composition comprising a compound of Formula (I), or a pharmaceutically acceptable salt thereof, and a pharmaceutically acceptable excipient (the composition preferably comprises a therapeutically effective amount of the compound or salt), for example, a pharmaceutical composition comprising a compound of Formula (II) or a pharmaceutically acceptable salt thereof or a pharmaceutical composition comprising a compound of Formula (III) or a pharmaceutically acceptable salt thereof, and a pharmaceutically acceptable excipient;

a method for treating a disease or condition in an animal in need thereof, e.g., a mammal such as a human, wherein a $5\text{-HT}_{2C}$ receptor is implicated and modulation of a $5\text{-HT}_{2C}$-associated function is desired comprising administering a therapeutically effective amount of a compound of Formula (I), e.g., a compound of Formula (II) or a compound of Formula (III), or a pharmaceutically acceptable salt thereof to the animal;

a method for treating or preventing a disease or disorder of the central nervous system in an animal in need thereof comprising administering a therapeutically effective amount of a compound of Formula (I), e.g., a compound of Formula (II) or a compound of Formula (III), or a pharmaceutically acceptable salt thereof to the animal;

a compound of Formula (I), e.g., a compound of Formula (II) or a compound of Formula (III), or a pharmaceutically acceptable salt thereof for use in medical diagnosis or therapy (e.g. the treatment or prevention of 5-HT related disease such as anxiety, obesity, depression, or a stress related disease);

the use of a compound of Formula (I), e.g., a compound of Formula (II) or a compound of Formula (III), or a pharmaceutically acceptable salt thereof to prepare a medicament useful for treating or preventing a disease or disorder of the central nervous system in an animal in need thereof;

the use of a compound of Formula (I), e.g., a compound of Formula (II) or a compound of Formula (III), or a pharmaceutically acceptable salt thereof as an imaging agent or as a biomarker for medical therapy and diagnosis;

a method of imaging tissue comprising 5-HT receptor comprising contacting the tissue with a radiolabeled compound of Formula (I), Formula (II) or Formula (III) or pharmaceutically acceptable salts thereof, and detecting the compound bound to said tissue; and a method for modulating $5\text{-HT}_{2C}$ receptor function, comprising administering an effective modulatory amount of a compound of Formula (I), e.g., a compound of Formula (II) or a compound of Formula (III), or a pharmaceutically acceptable salt thereof.

The invention also provides novel intermediates and processes disclosed herein that are useful for preparing compounds of Formula (I), e.g., a compound of Formula (II) or a compound of Formula (III).

DETAILED DESCRIPTION OF THE INVENTION

The compounds of the invention are useful for treating or preventing diseases or disorders of the central nervous system. Specific diseases or disorders include, but are not limited to: epilepsy, cyclothymic disorder, dysthymic disorder, fibromyalgia and other somatoform disorders, Alzheimers disease, neurodegenerative disorders, autism, chemotherapy-induced vomiting, "poop out" syndrome, peripheral neuropathy, a specific development disorder, obesity, obsessive compulsive disorder, anorexia nervosa, bulimia nervosa, depression, immune system depression, addictive disorder and withdrawal syndrome, withdrawal from drug abuse, schizophrenia, schizophreniform disorder, schizoaffective disorder, delusional disorder, a phobia, bipolar disorder, a psychotic disorder (brief and long duration disorders, psychotic disorder due to medical condition, psychotic disorder NOS), mood disorder (major depressive or bipolar disorder with psychotic features) seasonal affective disorder, a stress related disease (e.g. general anxiety disorder), panic disorder, a stress induced problem with the urinary, gastrointestinal or cardiovascular system (e.g., stress incontinence), post-traumatic-stress syndrome, post-traumatic stress disorder, premenstrual dysphoric disorder, a sleep disorder, agitation disorder, headaches, migraine, cluster headaches, sexual dysfunction in a mammal (e.g. a human), an adjustment disorder, an age-associated learning and mental disorder, apathy, an attention-disorder due to general medical conditions, attention-deficit hyperactivity disorder, behavioral disturbance (including agitation in conditions associated with diminished cognition (e.g., dementia, mental retardation or delirium), chronic fatigue syndrome, conduct disorder, hypertension, anxiety, generalized anxiety disorder, an inhalation disorder, an intoxication disorder, movement disorder (e.g., Huntington's disease, Tardive Dyskinesia or Parkinson's Disease), a Tic disorder (e.g., Tourette syndrome), oppositional defiant disorder, and selective serotonin reuptake inhibition (SSRI).

A compound of the invention can directly or indirectly affect serotonin neurotransmission, e.g., as an agonist or partial agonist of a serotonin receptor, e.g., $5\text{-HT}_{2C}$. Specifically, a compound of the invention can be a $5\text{-HT}_{2C}$ partial agonist. In addition, a compound of the invention can be a "serotonergic agent", e.g., one that affects the activity and/or the availability of serotonin and/or its precursor, L-typtophan.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to.

Alkyl or alkylene can be partially unsaturated, e.g., the alkyl chain may comprise one or more (e.g. 1, 2, 3, or 4) double or triple bonds in the chain.

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, $C_{1-8}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. For the nitrogen containing heteroaryls, they can be linked at a ring carbon or a ring nitrogen which forms a stable compound. For example, a pyrrole group could be linked by the nitrogen atom or the 2,3, 4 or 5 carbon atom.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine 5-HT$_{2C}$ activity using the standard tests which are well known in the art.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-8}$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, $C_{1-8}$alkyl can be methyl, ethyl, propyl, isopropyl, butyl, iso-butyl, sec-butyl, pentyl, 3-pentyl, hexyl, or heptyl; $—OC_{1-8}$alkyl can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C_{1-8}$alkanoyl can be acetyl, propanoyl, butanoyl, pentanoyl, 4-methylpentanoyl, hexanoyl or heptanoyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for Z is —CH$_2$—, —O—, —N(R$_a$)—, —S—, —SO—, or —SO$_2$—.

A specific value for Z is —S—, —SO—, or —SO$_2$—.

A specific value for Z is —O— or —N(R$_a$)—.

A specific value for Z is —O—.

A specific value for Z is —N(CH$_3$)—.

A specific value for Z is —N(benzyl)-.

A specific value for $R^1$ is H, $C_{1-6}$alkyl, or aryl$C_{1-8}$alkylene-.

A specific value for $R^1$ is H, $C_{1-6}$alkyl, or —(CH$_2$) aryl.

A specific value for $R^1$ is $C_{1-6}$alkyl, or benzyl.

A specific value for $R^1$ is H, methyl, ethyl, propyl or butyl.

A more specific value for $R^1$ is H, methyl or ethyl.

A specific value for $R^2$ is $C_{1-8}$alkyl, aryl, aryl$C_{1-8}$alkylene-, OH, or —OC$_{1-8}$alkyl.

A specific value for $R^2$ is methyl, ethyl, propyl, OH, methoxy, ethoxy, phenyl, or benzyl.

A specific value for $R^2$ is methyl, ethyl, OH, methoxy, phenyl, or benzyl.

A specific value for p is 0, 1, or 2.

A specific value for $R^3$ is H, $C_{1-6}$alkyl and aryl$C_{1-8}$alkylene-.

A specific value for $R^3$ is H, methyl, ethyl, propyl or benzyl.

A specific value for $R^3$ is H, methyl, ethyl, or benzyl.

A specific value for $R^4$ is H, $C_{1-8}$ alkyl, aryl, aryl$C_{1-8}$alkylene-, or fluoro.

A specific value for $R^4$ is H, methyl, ethyl, propyl, butyl, 2-phenylethyl or benzyl.

A specific value for $R^4$ is H, methyl, ethyl, propyl or benzyl.

A specific value for $R^4$ is methyl, ethyl or benzyl. A specific value for $R^5$ is H, $C_{1-6}$alkyl, aryl, or aryl$C_{1-8}$ alkylene.

A specific value for $R^5$ is H or phenyl optionally substituted with 1, 2, or 3 substituents, wherein the substituents are fluoro, chloro, bromo, —CF$_3$, —OCF$_3$, —OC$_{1-6}$alkyl, —NR$_c$R$_d$, or C$_{1-6}$alkyl.

A specific value for $R^5$ is phenyl optionally substituted with 1 or 2 substituents, wherein the substituents are fluoro, chloro, bromo, —CF$_3$, —OCF$_3$, —OC$_{1-6}$alkyl, —NR$_c$R$_d$, or C$_{1-6}$alkyl.

A specific value for $R^5$ is 2,4-dichlorophenyl or 2,6-difluorophenyl.

A specific value for $R^6$ is H, $C_{1-6}$alkyl, aryl, or aryl$C_{1-8}$ alkylene.

A specific value for $R^6$ is H, or phenyl optionally substituted with 1, 2, or 3 substituents, wherein the substituents are fluoro, chloro, bromo, —CF$_3$, —OCF$_3$, —OC$_{1-6}$alkyl, —NR$_c$R$_d$, or C$_{1-6}$alkyl.

A specific value for $R^6$ is phenyl optionally substituted with 1 or 2 substituents independently selected from fluoro, chloro, bromo, —CF$_3$, —OCF$_3$, —OC$_{1-6}$alkyl, —NR$_c$R$_d$ and C$_{1-6}$alkyl.

A specific value for $R^6$ is 2,4-dichlorophenyl or 2,6-difluorophenyl.

Specifically, the invention also provides a method for treating or preventing anxiety, depression, schizophrenia, epilepsy, migraine, Alzheimer's disease, sleep disorders, obesity, diseases that may be associated with a stress induced problem with the gastrointestinal or cardiovascular system, sexual dysfunction, and withdrawal from drug abuse comprising administering a therapeutically effective amount of a compound of Formula (I), e.g., a compound of Formula (II) or Formula (III), or a pharmaceutically acceptable salt thereof to the mammal.

Specifically, the invention also provides the use of a compound of Formula (I), e.g., Formula (II) or Formula (III), or a pharmaceutically acceptable salt thereof to prepare a medicament for treating or preventing anxiety, depression, schizophrenia, epilepsy, migraine, Alzheimer's disease, sleep disorders, obesity, diseases that may be associated with a stress induced problem with the gastrointestinal or cardiovascular system, sexual dysfunction, or withdrawal from drug abuse.

Specifically, the invention also provides the use of a compound of Formula (I), e.g., Formula (II) or Formula (III), or a pharmaceutically acceptable salt thereof to prepare a medicament for treating or preventing anxiety, depression and/or obesity.

Compounds of Formula (I), Formula (II) and Formula (III) are 5-HT ligands. Thus, radiolabeled compounds of Formula (I), Formula (II) and Formula (III) are useful as imaging agents or as a biomarker for medical therapy and diagnosis. Such radiolabeled compounds are also useful as pharmacological tools for studying 5-HT function and activity. Accordingly, the invention also provides a radiolabeled compound of Formula (I), Formula (II), Formula (III) or salts thereof.

Compounds of Formula (I), Formula (II) and Formula (III) or pharmaceutically acceptable salts thereof can be labeled using techniques which are well known in the art. For example, a radioisotope can be incorporated into the compound or appended to the compound of Formula (I), Formula (II), Formula (III) or pharmaceutically acceptable salts thereof, using techniques well known in the art. For example, see Arthur Murry III, D. Lloyd Williams; *Organic Synthesis with Isotopes*, vol. I and II, Interscience Publishers Inc., N.Y. (1958) and Melvin Calvin et al., *Isotopic Carbon*, John Wiley and Sons Inc., N.Y. (1949). Any radioisotope capable of being detected can be employed as a label. For example, suitable radioisotopes include: carbon-11, fluorine-18, fluorine-19, iodine-123 and iodine-125. Preferably, a compound of Formula (I), Formula (II), Formula (III) or pharmaceutically acceptable salts thereof, may be labeled by appending one or more radioisotopes of a halogen (e.g. iodine-123) to an aromatic ring, or by alkylating a nitrogen of a compound of Formula (I), Formula (II), Formula (III) or pharmaceutically acceptable salts thereof, with a group comprising a phenyl group bearing a radioisotope.

The invention also provides a method for preparing a compound of Formula (I), Formula (II) and Formula (III) wherein $R^1$ is hydrogen comprising deprotecting a corresponding compound of Formula (I) wherein $R^1$ is a suitable nitrogen protecting group.

Representative compounds of the invention can generally be prepared using the synthetic procedures illustrated in Schemes 1–4. Starting materials can be prepared by procedures described in these schemes, or by procedures that are well known to one of ordinary skill in organic chemistry. The variables used in the Schemes are as defined herein.

In Schemes 1 and 2, where Z is not CH, and q is 1, 2, or 3. The intermediate 3 can be prepared as illustrated in Scheme 1. Starting from the commercially available material, 2,6-dichloro-3-nitropyridine, 1a, compound 1 is obtained by a procedure described in the literature, proceeding through pyridine ester, 1b, (see, German Patent Publication DD 235 262 A1, published Apr. 30, 1986). Reductive removal of the lactam carbonyl with borane provides the bicyclic amine, 2. The amine is converted to the corresponding hydrazine, 3, by treatment with amyl nitrite followed by lithium aluminum hydride reduction.

The compounds of Formula (I), Formula (II) and Formula (III) can be prepared as illustrated in Scheme 2. A Fischer indole synthesis using hydrazine, 3, and a ketone, such as 4-piperidone, 4, is carried out in 85% phosphoric acid to provide an indole (see, *Indoles, Best Synthetic Methods*, Academic Press, San Diego, Calif. (1999)). The indole is protected using the Boc protecting group in a one-pot reaction to provide the protected indole, 5 (see *Protective Groups in Organic Synthesis*, 3rd ed., Greene and Wuts, John Wiley and Sons, Inc., New York (1999)). The protected indole, 5, is treated with a metallated aromatic reagent (e.g., B, Sn, Al, Zn, Mg, etc.) such as an aryl boronic acid under palladium catalysis (such as Pd(PPh$_3$)$_4$, Pd$_2$(dba)$_3$, Pd(OAc)$_2$, etc.) to form the arylated indole, 6, (see Miyaura et al., *Chem Rev.*, 95, 2457 (1995)). Removal of the protecting group with acidic treatment provides the arylated tetracyclic amine, 7. Reduction of amine, 7, with sodium cyanoborohydride in an acidic media, e.g., trifluoroacetic acid or acetic acid, provides the indoline, 8 ($R^1$=H). Amine (indole), 7, or amine (indoline), 8, can be derivatized using standard reductive alkylation conditions, e.g., treatment with an aldehyde in the presence of sodium cyanoborohydride (see, for example, Lane, "Sodium Cyanoborohydride—A Highly Selective Reducing Agent for Organic Functional Groups", *Synthesis*, 135 (1975) to give the $R^1$ substituted products, e.g., 8, as desired.

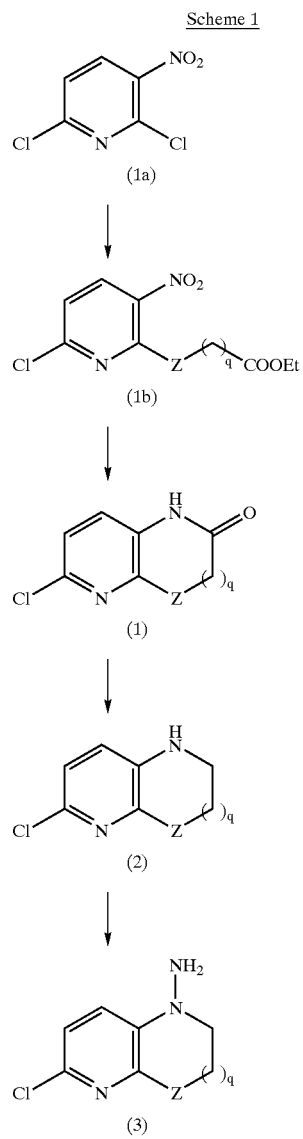

Scheme 1

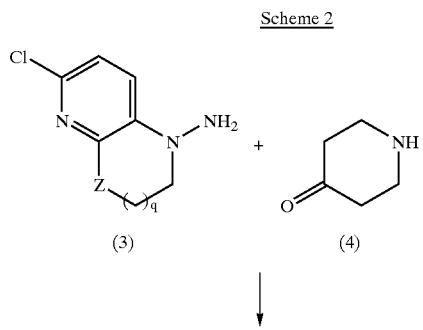

Scheme 2

-continued

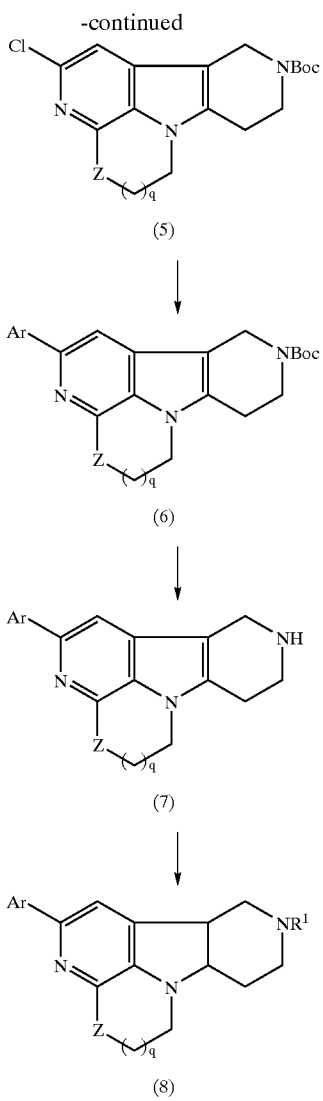

(5)

(6)

(7)

(8)

The intermediates, where Z is carbon or carbonyl, can be prepared as described in Scheme 3 and Scheme 4. When q=0 (Scheme 3), the halogen intermediate 12 can be obtained from 11 (see *Chem. Abst.* 1978, 37665) by reduction with a reducing agent such as sodium cyanoborohydride in an acid media such as trifluoroacetic acid or acetic acid.

Scheme 3

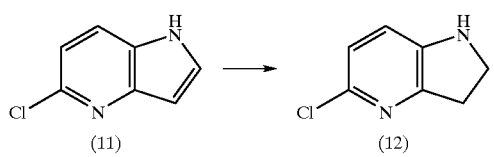

(11)  (12)

When q=1 (Scheme 4), the starting material 13 can be obtained by following the procedures described in *J. Org. Chem.*, 1963, 28. 1753. When q=2 (Scheme 4), the starting material 13 can be obtained by following the procedures described in *J. Heterocyclic Chem.*, 2000, 41. Compound 13 can be oxidized to the ketone compound 14 by following the procedures described in the last mentioned literature. In compound 14, the nitrogen can be protected with, for example, a Boc group, and the ketone can be protected with ethylene glycol to form a ketal. Treatment of compound 14 with a strong base such as the complex of butylithium/Me$_2$N (CH$_2$)$_2$OLi followed by quenching the generated anion with an electrophile such as carbon tetrabromide (see, *J. Chem. Soc. Perkin Trans.*, 1 1997, 3597) provides the bromo compound 16 (Y=Br), in which the protecting group can be removed by treatment with acids such as hydrochloric acid. The carbonyl group in compound 17 can be converted into the methylene group by carrying out a Wolff-Kishner reaction under the conditions H$_2$NNH$_2$/KOH/diethylene glycol. The intermediates 12, 17 and 18 can be converted into the corresponding hydrazine compound 3 (Scheme 1) using the same conditions as described herein for the Z is heteroatom compounds.

Scheme 4

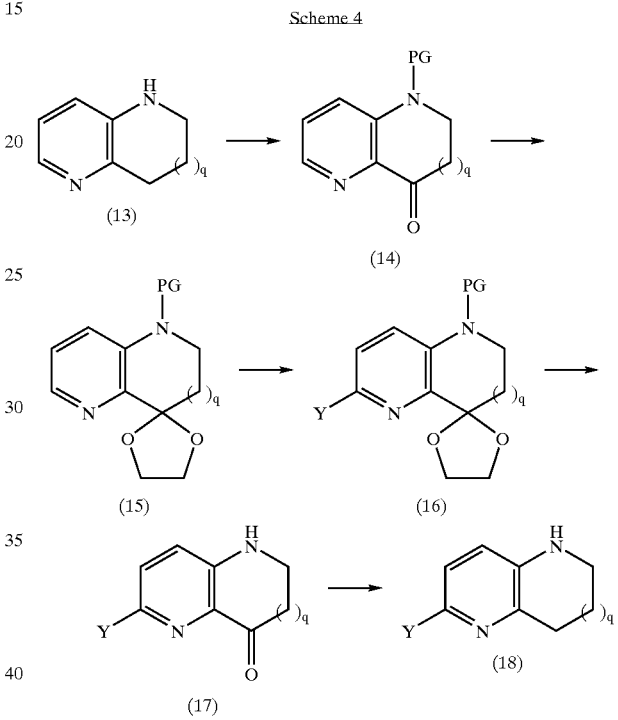

(13)  (14)

(15)  (16)

(17)  (18)

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is *Remington's Pharmaceutical Sciences*, 15th ed., E. W. Martin, Mark Publ. Co., (1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of Formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT2C receptor agonist or a partial antagonist can also be determined using in vitro and in vivo assays that are known in the art. The invention provides compounds of Formula (I) that act as either agonists or as antagonists of one or more 5-HT receptor subtypes. The compounds of the invention are 5-HT ligands, which displace a radiolabeled test ligand from one or more 5-HT receptor subtype at a concentration of 1 mM. The procedures used for testing such displacement are well known and would be readily available to one skilled in the art. For example, see Fitzgerald et al., *Mol. Pharmacol*, 57, 1, 75–81 (2000); and Wainscott, et al., *J. Pharmacol Exp Ther.*, 276, 2, 720–727 (1996).

DESCRIPTION OF PREFERRED EMBODIMENTS

The following compounds can be made according to the description and schemes described herein.

2-Phenyl-5,6,6b,7,8,9,10,10a-octahydro-4-oxa-3,6a,9-triaza-fluoranthene:

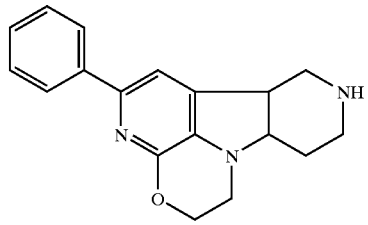

2-(2,6-Difluorophenyl)-5,6,6b,7,8,9,10,10a-octahydro-4-oxa-3,6a,9-triazafluoranthene:

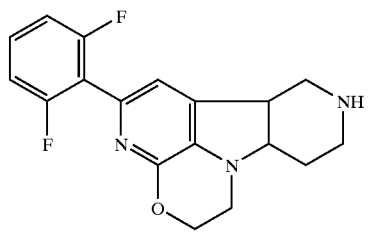

2-(2,4-Dichlorophenyl)-5,6,6b,7,8,9,10,10a-octahydro-4-oxa-3,6a,9-triazafluoranthene:

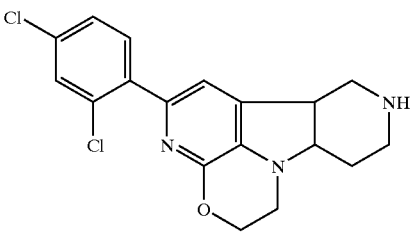

2-Phenyl-6,7,7b,8,9,10,11,11a-octahydro-5H-4-thia-3,7a,10-triazacyclohepta[jk]fluorene:

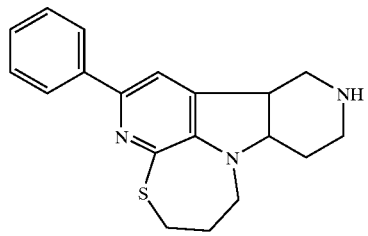

2-(2,4-Dichlorophenyl)-6,7,7b,8,9,10,11,11a-octahydro-5H-4-thia-3,7a,10-triazacyclohepta[jk]fluorene:

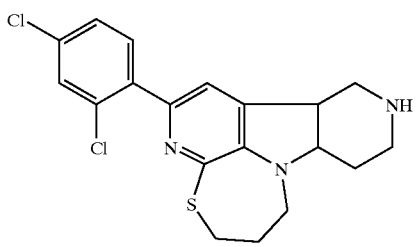

and
2-(2,6-Difluorophenyl)-6,7,7b,8,9,10,11,11a-octahydro-5H-4-thia-3,7a,10-triazacyclohepta[jk]fluorene:

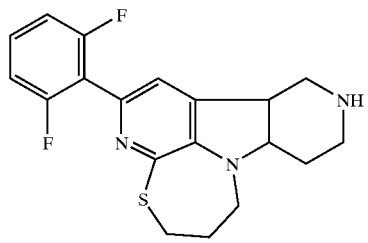

The invention has been described with reference to various specific and preferred embodiments and techniques. However, it should be understood that many variations and modifications may be made while remaining within the spirit and scope of the invention.

What is claimed:
1. A compound of Formula (I):

Formula I

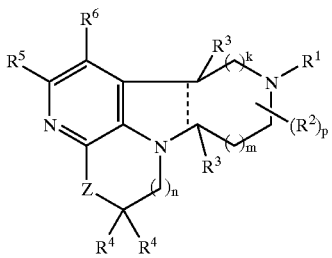

wherein Z is —O—;
the bond represented by - - - is a single or double bond;
$R^1$ is H, $C_{1-8}$alkyl, $C_{3-8}$cycloalkyl, or aryl$C_{1-8}$alkylene-;
each $R^2$ is independently $C_{1-8}$ alkyl, aryl, aryl$C_{1-8}$alkylene-, or $OR_a$;
each $R^3$ is absent or independently H, $C_{1-8}$ alkyl, aryl$C_{1-8}$alkylene-, provided that each $R^3$ is absent when the bond represented by - - - is a double bond;

each $R^4$ is independently H, —F, $C_{1-8}$ alkyl, aryl, aryl$C_{1-8}$alkylene-, heteroaryl, or heteroaryl($C_{1-8}$)alkylene-;

$R^5$ and $R^6$ are each independently H, halo, —CN, —NO$_2$, —CF$_3$, —OCF$_3$, azido, —OR$_a$, —NR$_c$R$_d$, —C(=O)NR$_c$R$_d$, —C(=S)NR$_c$R$_d$, $C_{1-8}$ alkyl, $C_{3-8}$ cycloalkyl, aryl, aryl$C_{1-8}$alkylene-, heteroaryl, heteroaryl$C_{1-8}$alkylene-, amidinyl, guanidinyl, thioguanidinyl, or cyanoguanidinyl;

wherein any aryl or heteroaryl group of $R^1$, $R^2$, $R^3$, $R^4$, $R^5$, and $R^6$ is optionally substituted with up to 4 substituents independently selected from the following: halo, —OH, —CN, —NO$_2$, —CF$_3$, —OCF$_3$, N$_3$, —S(O)$_{0-2}$C$_{1-8}$alkyl, —C$_{1-8}$alkyl, —C$_{3-8}$cycloalkyl, —OC$_{1-8}$alkyl, phenyl, —C$_{1-8}$alkanoyl, —C(=O)OR$_a$, —N(R$_a$)C(=O)NR$_c$R$_d$, —N(R$_a$)C(=O)OR$_a$, —C(=O)NR$_c$R$_d$, —C(=S)NR$_c$R$_d$, —SO$_2$NR$_c$R$_d$, —C$_{1-8}$alkyl, —NR$_c$R$_d$, —OPh, tetrazolyl, triazolyl, amidinyl, guanidinyl, thioguanidinyl, and cyanoguanidinyl;

R$_a$ and R$_b$ are each independently H, C$_{1-8}$alkyl, —C$_{3-8}$cycloalkyl, aryl, aryl(C$_{1-8}$)alkylene-, heteroaryl, or heteroaryl(C$_{1-8}$)alkylene-;

R$_c$ and R$_d$ are each independently H, C$_{1-8}$alkyl, —C$_{3-8}$cycloalkyl, aryl, aryl(C$_{1-8}$)alkylene-, heteroaryl, or heteroaryl(C$_{1-8}$)alkylene-; or R$_c$ and R$_d$ together with the nitrogen to which they are attached form a pyrrolidine, piperidine, azepine, morpholine, thiomorpholine, thiomorpholine 1-oxide, or thiomorpholine 1,1-dioxide ring;

k is 1 or 2;

m is 1;

n is 1;

p is 0, 1, 2, 3, 4, 5, 6, 7, 8, 9, or 10;

or a pharmaceutically acceptable salt thereof.

2. The compound of claim 1, which is a compound of Formula (II):

Formula II wherein Z is —O—;

$R^1$ is H, C$_{1-8}$alkyl, C$_{3-8}$cycloalkyl, or arylC$_{1-8}$alkylene-;

each $R^2$ is independently C$_{1-8}$ alkyl, aryl, arylC$_{1-8}$alkylene-, or OR$_a$;

each $R^3$ is independently H, C$_{1-8}$ alkyl or arylC$_{1-8}$alkylene-;

each $R^4$ is independently H, —F, C$_{1-8}$ alkyl, aryl, arylC$_{1-8}$alkylene-, heteroaryl, or heteroaryl(C$_{1-8}$)alkylene-;

$R^5$ and $R^6$ are each independently H, halo, —CN, —NO$_2$, —CF$_3$, —OCF$_3$, azido, —OR$_a$, —NR$_c$R$_d$, —C(=O)NR$_c$R$_d$, —C(=S)NR$_c$R$_d$, C$_{1-8}$ alkyl, C$_{3-8}$ cycloalkyl, aryl, arylC$_{1-8}$alkylene-, heteroaryl, heteroarylC$_{1-8}$alkylene-, amidinyl, guanidinyl, thioguanidinyl, or cyanoguanidinyl;

wherein any aryl or heteroaryl group of $R^1$, $R^2$, $R^3$, $R^4$, $R^5$, and $R^6$ is optionally substituted with up to 4 substituents independently selected from the following: halo, —OH, —CN, —NO$_2$, —CF$_3$, —OCF$_3$, N$_3$, —S(O)$_{0-2}$C$_{1-8}$alkyl, —C$_{1-8}$alkyl, —C$_{3-8}$cycloalkyl, —OC$_{1-8}$alkyl, phenyl, —C$_{1-8}$alkanoyl, —C(=O)OR$_a$, —N(R$_a$)C(=O)NR$_c$R$_d$, —N(R$_a$)C(=O)OR$_a$, —C(=O)NR$_c$R$_d$, —C(=S)NR$_c$R$_d$, —SO$_2$NR$_c$R$_d$, —C$_{1-8}$alkyl, —NR$_c$R$_d$, —OPh, tetrazolyl, triazolyl, amidinyl, guanidinyl, thioguanidinyl, and cyanoguanidinyl;

R$_a$ and R$_b$ are each independently H, C$_{1-8}$alkyl, —C$_{3-8}$cycloalkyl, aryl, aryl(C$_{1-8}$)alkylene-, heteroaryl, or heteroaryl(C$_{1-8}$)alkylene-;

R$_c$ and R$_d$ are each independently H, C$_{1-8}$alkyl, —C$_{3-8}$cycloalkyl, aryl, aryl(C$_{1-8}$)alkylene-, heteroaryl, or heteroaryl(C$_{1-8}$)alkylene-; or R$_c$ and R$_d$ together with the nitrogen to which they are attached form a pyrrolidine, piperidine, azepine, morpholine, thiomorpholine, thiomorpholine 1-oxide, or thiomorpholine 1,1-dioxide ring;

k is 1 or 2;

m is 1;

n is 1;

p is 0, 1, 2, 3, 4, 5, 6, 7, 8, 9, or 10;

or a pharmaceutically acceptable salt thereof.

3. The compound of claim 2, wherein $R^1$ is H, —C$_{1-6}$alkyl, or arylC$_{1-8}$alkylene-.

4. The compound of claim 3, wherein $R^1$ is H, —C$_{1-6}$alkyl, or —(CH$_2$)-aryl.

5. The compound of claim 4, wherein $R^1$ is C$_{1-6}$alkyl or benzyl.

6. The compound of claim 3, wherein $R^1$ is H, methyl, ethyl, propyl or butyl.

7. The compound of claim 6, wherein $R^1$ is H, methyl or ethyl.

8. The compound of claim 2, wherein $R^2$ is C$_{1-8}$alkyl, aryl, arylC$_{1-8}$alkylene-, —OH, or —OC$_{1-8}$alkyl.

9. The compound of claim 8, wherein $R^2$ is methyl, ethyl, propyl, —OH, methoxy, ethoxy, phenyl, or benzyl.

10. The compound of claim 8, wherein $R^2$ is methyl, ethyl, —OH, methoxy, phenyl, or benzyl.

11. The compound of claim 8, wherein p is 0, 1, or 2.

12. The compound of claim 2, wherein $R^3$ is H, C$_{1-6}$alkyl and arylC$_{1-8}$alkylene-.

13. The compound of claim 12, wherein $R^3$ is H, methyl, ethyl, propyl or benzyl.

14. The compound of claim 12, wherein $R^3$ is H, methyl, ethyl, or benzyl.

15. The compound of claim 2, wherein $R^4$ is H, C$_{1-8}$ alkyl, aryl, arylC$_{1-8}$alkylene-, or —F.

16. The compound of claim 15, wherein $R^4$ is H, methyl, ethyl, propyl, butyl, 2-phenylethyl, or benzyl.

17. The compound of claim 15, wherein $R^4$ is H, methyl, ethyl, propyl or benzyl.

18. The compound of claim 15, wherein $R^4$ is methyl, ethyl or benzyl.

19. The compound of claim 2, wherein $R^5$ and $R^6$ are each independently H, C$_{1-6}$alkyl, aryl, or arylC$_{1-8}$alkylene-.

20. The compound of claim 19, wherein $R^5$ and $R^6$ are each independently H, or phenyl optionally substituted with 1, 2, or 3 substituents independently selected from —F, —Cl, —Br, —CF$_3$, —OCF$_3$, —OC$_{1-6}$alkyl, —NR$_c$R$_d$, or —C$_{1-6}$alkyl.

21. The compound of claim 19, wherein $R^5$ is phenyl optionally substituted with 1, 2, or 3 substituents independently selected from —F, —Cl, —Br, —CF$_3$, —OCF$_3$, —OC$_{1-6}$alkyl, —NR$_c$R$_d$, or —C$_{1-6}$alkyl.

22. The compound of claim 19, wherein $R^6$ is phenyl optionally substituted with 1, 2, or 3 substituents independently selected from —F, —Cl, —Br, —CF$_3$, —OCF$_3$, —OC$_{1-6}$alkyl, —NR$_c$R$_d$, or —C$_{1-6}$alkyl.

23. The compound of claim 19, wherein $R^5$ is 2,4-dichlorophenyl or 2,6-difluorophenyl.

24. The compound of claim 19, wherein $R^6$ is 2,4-dichlorophenyl or 2,6-difluorophenyl.

25. The compound of claim 2, wherein the compound is
2-phenyl-5,6,6b,7,8,9,10,10a-octahydro-4-oxa-3,6a,9-triazafluoranthene;
2-(2,6-difluorophenyl)-5,6,6b,7,8,9,10,10a-octahydro-4-oxa-3,6a,9-triaza-fluoranthene;
2-(2,4-dichlorophenyl)-5,6,6b,7,8,9,10,10a-octahydro-4-oxa-3,6a,9-triaza-fluoranthene;
or a pharmaceutically acceptable salt thereof.

26. A pharmaceutical composition comprising a compound of claim 2 and a pharmaceutically acceptable excipient.

27. A pharmaceutical composition comprising a compound of claim 25 and a pharmaceutically acceptable excipient.

28. A method for treating a disease or condition of the central nervous system in a mammal comprising administering a therapeutically effective amount of a compound of claim 2, wherein the disease or condition of the central nervous system is selected from the group consisting of anxiety, obesity, depression, obsessive compulsive disorder, phobias, psychiatric syndromes and migraine.

29. A method for treating a disease or condition of the central nervous system in a mammal comprising administering a therapeutically effective amount of a compound of claim 25, wherein the disease or condition of the central nervous system is selected from the group consisting of anxiety, obesity, depression, obsessive compulsive disorder, phobias, psychiatric syndromes and migraine.

30. The compound of claim 1, which is a compound of Formula (III):

Formula III wherein Z is —O—;
$R^1$ is H, C$_{1-8}$alkyl, C$_{3-8}$cycloalkyl, or arylC$_{1-8}$alkylene-;
each $R^2$ is independently C$_{1-8}$ alkyl, aryl, arylC$_{1-8}$alkylene-, or OR$_a$;
each $R^4$ is independently H, —F, C$_{1-8}$ alkyl, aryl, arylC$_{1-8}$alkylene-, heteroaryl, or heteroaryl(C$_{1-8}$)alkylene-;
$R^5$ and $R^6$ are each independently H, halo, —CN, —NO$_2$, —CF$_3$, —OCF$_3$, azido, —OR$_a$, —NR$_c$R$_d$, —C(=O)NR$_c$R$_d$, —C(=S)NR$_c$R$_d$, C$_{1-8}$ alkyl, C$_{3-8}$ cycloalkyl, aryl, arylC$_{1-8}$alkylene-, heteroaryl, heteroarylC$_{1-8}$alkylene-, amidinyl, guanidinyl, thioguanidinyl, or cyanoguanidinyl;
wherein any aryl or heteroaryl group of $R^1$, $R^2$, $R^3$, $R^4$, $R^5$, and $R^6$ is optionally substituted with up to 4 substituents independently selected from the following: halo, —OH, —CN, —NO$_2$, —CF$_3$, —OCF$_3$, N$_3$, —S(O)$_{0-2}$C$_{1-8}$alkyl, —C$_{1-8}$alkyl, —C$_{3-8}$cycloalkyl, —OC$_{1-8}$alkyl, phenyl, —C$_{1-8}$alkanoyl, —C(=O)OR$_a$, —N(R$_a$)C(=O)NR$_c$R$_d$, —N(R$_a$)C(=O)OR$_a$, —C(=O)NR$_c$R$_d$, —C(=S)NR$_c$R$_d$, —SO$_2$NR$_c$R$_d$, —C$_{1-8}$alkyl, —NR$_c$R$_d$, —OPh, tetrazolyl, triazolyl, amidinyl, guanidinyl, thioguanidinyl, and cyanoguanidinyl;
$R_a$ and $R_b$ are each independently H, C$_{1-8}$alkyl, —$_{3-8}$cycloalkyl, aryl, aryl(C$_{1-8}$)alkylene-, heteroaryl, or heteroaryl(C$_{1-8}$) alkylene-;
$R_c$ and $R_d$ are each independently H, C$_{1-8}$alkyl, —C$_{3-8}$cycloalkyl, aryl, aryl(C$_{1-8}$)alkylene-, heteroaryl, or heteroaryl(C$_{1-8}$)alkylene-; or $R_c$ and $R_d$ together with the nitrogen to which they are attached form a pyrrolidine, piperidine, azepine, morpholine, thiomorpholine, thiomorpholine 1-oxide, or thiomorpholine 1,1-dioxide ring;
k is 1 or 2;
m is 1;
n is 1;
p is 0, 1, 2, 3, 4, 5, 6, 7, 8, 9, or 10;
or a pharmaceutically acceptable salt thereof.

31. The compound of claim 30, wherein $R^1$ is H, —C$_{1-6}$alkyl, or arylC$_{1-8}$alkylene-.

32. The compound of claim 31, wherein $R^1$ is H, —C$_{1-6}$alkyl, or —(CH$_2$)-aryl.

33. The compound of claim 32, wherein $R^1$ is C$_{1-6}$alkyl or benzyl.

34. The compound of claim 31, wherein $R^1$ is H, methyl, ethyl, propyl or butyl.

35. The compound of claim 34, wherein $R^1$ is H, methyl or ethyl.

36. The compound of claim 30, wherein $R^2$ is C$_{1-8}$alkyl, aryl, arylC$_{1-8}$alkylene-, —OH, or —OC$_{1-8}$alkyl.

37. The compound of claim 36, wherein $R^2$ is methyl, ethyl, propyl, —OH, methoxy, ethoxy, phenyl, or benzyl.

38. The compound of claim 36, wherein $R^2$ is methyl, ethyl, —OH, methoxy, phenyl, or benzyl.

39. The compound of claim 36, wherein p is 0, 1, or 2.

40. The compound of claim 30, wherein $R^3$ is H, C$_{1-6}$alkyl and arylC$_{1-8}$alkylene-.

41. The compound of claim 40, wherein $R^3$ is H, methyl, ethyl, propyl or benzyl.

42. The compound of claim 40, wherein $R^3$ is H, methyl, ethyl, or benzyl.

43. The compound of claim 30, wherein $R^4$ is H, C$_{1-8}$ alkyl, aryl, arylC$_{1-8}$alkylene-, or —F.

44. The compound of claim 43, wherein $R^4$ is H, methyl, ethyl, propyl, butyl, 2-phenylethyl, or benzyl.

45. The compound of claim 43, wherein $R^4$ is H, methyl, ethyl, propyl or benzyl.

46. The compound of claim 43, wherein $R^4$ is methyl, ethyl or benzyl.

47. The compound of claim 30, wherein $R^5$ and $R^6$ are each independently H, C$_{1-6}$alkyl, aryl, or arylC$_{1-8}$alkylene-.

48. The compound of claim 47, wherein $R^5$ and $R^6$ are each independently H, or phenyl optionally substituted with 1, 2, or 3 substituents independently selected from —F, —Cl, —Br, —CF$_3$, —OCF$_3$, —OC$_{1-6}$alkyl, —NR$_c$R$_d$, or —C$_{1-6}$alkyl.

49. The compound of claim 47, wherein $R^5$ is phenyl optionally substituted with 1, 2, or 3 substituents independently selected from —F, —Cl, —Br, —CF$_3$, —OCF$_3$, —OC$_{1-6}$alkyl, —NR$_c$R$_d$, or —C$_{1-6}$alkyl.

50. The compound of claim 47, wherein $R^6$ is phenyl optionally substituted with 1, 2, or 3 substituents independently selected from —F, —Cl, —Br, —CF$_3$, —OCF$_3$, —OC$_{1-6}$alkyl, —NR$_c$R$_d$, or —C$_{1-6}$alkyl.

51. The compound of claim 47, wherein R$^5$ is 2,4-dichlorophenyl or 2,6-difluorophenyl.

52. The compound of claim 47, wherein R$^6$ is 2,4-dichlorophenyl or 2,6-difluorophenyl.

53. A pharmaceutical composition comprising a compound of claim 30 and a pharmaceutically acceptable excipient.

54. A method for treating a disease or condition of the central nervous system in a mammal comprising administering a therapeutically effective amount of a compound of claim 30, wherein the disease or condition of the central nervous system is selected from the group consisting of anxiety, obesity, depression, obsessive compulsive disorder, phobias, psychiatric syndromes and migraine.

* * * * *